US010730688B2

(12) United States Patent
Reed et al.

(10) Patent No.: US 10,730,688 B2
(45) Date of Patent: Aug. 4, 2020

(54) DISPENSER FOR PARTICULATE MATERIAL

(71) Applicant: ESSENTRA FILTER PRODUCTS DEVELOPMENT CO. PTE. LTD, Singapore (SG)

(72) Inventors: James Reed, Newcastle (GB); Paul Clarke, Northumberland (GB); Evgenia Menon, Newcastle upon Tyne (GB); Gary Fulcher, Newcastle (GB); Lee O'Donovan, South Shields (GB)

(73) Assignee: ESSENTRA FILTER PRODUCTS DEVELOPMENT CO. PTE. LTD, Singapore (SG)

( * ) Notice: Subject to any disclaimer, the term of this patent is extended or adjusted under 35 U.S.C. 154(b) by 527 days.

(21) Appl. No.: 14/895,392

(22) PCT Filed: Jun. 2, 2014

(86) PCT No.: PCT/EP2014/061315
§ 371 (c)(1),
(2) Date: Dec. 2, 2015

(87) PCT Pub. No.: WO2014/195247
PCT Pub. Date: Dec. 11, 2014

(65) Prior Publication Data
US 2016/0114964 A1    Apr. 28, 2016

(30) Foreign Application Priority Data

Jun. 3, 2013 (GB) .................................. 1309923.9
Jul. 24, 2013 (GB) .................................. 1313251.9
Apr. 30, 2014 (GB) .................................. 1407617.8

(51) Int. Cl.
B65D 83/06    (2006.01)
A61M 15/06    (2006.01)
(Continued)

(52) U.S. Cl.
CPC .............. *B65D 83/06* (2013.01); *A24B 13/00* (2013.01); *A24D 3/0225* (2013.01); *A24F 23/00* (2013.01);
(Continued)

(58) Field of Classification Search
CPC ............................. B65D 83/06; A61M 15/06
(Continued)

(56) References Cited

U.S. PATENT DOCUMENTS

| 291,638 | A | * | 1/1884 | Story | B65D 39/00 |
| | | | | | 215/355 |
| 395,243 | A | * | 12/1888 | Maggi | A22C 17/10 |
| | | | | | 131/367 |

(Continued)

FOREIGN PATENT DOCUMENTS

| DE | 31 09 322 A1 | 10/1982 |
| EP | 0 150 810 A3 | 8/1985 |

(Continued)

OTHER PUBLICATIONS

"Bulk Density Chart." Anval. Web. Accessed Apr. 26, 2017. http://www.anval.net/downloads/bulk%20density%20chart.pdf.*
(Continued)

*Primary Examiner* — Eric Yaary
*Assistant Examiner* — Russell E Sparks
(74) *Attorney, Agent, or Firm* — Flynn Thiel, P.C.

(57) ABSTRACT

A particulate material dispenser including a longitudinally extending body having a longitudinally extending base element; a tubular element extending longitudinally from the base element such that an inner wall of the tubular element defines a first cavity; a capping element which is distanced longitudinally from an end of the tubular element; a common outer wrapper which is engaged around the base element, the tubular element and the capping element, the
(Continued)

inner wall of the common outer wrapper defining a second cavity between the tubular element and the capping element; and snuff within both the first cavity and the second cavity. The base element and/or the tubular element is porous.

8 Claims, 3 Drawing Sheets

(51) Int. Cl.
| | |
|---|---|
| *A24F 23/00* | (2006.01) |
| *B65D 71/06* | (2006.01) |
| *B65D 75/04* | (2006.01) |
| *B65D 75/58* | (2006.01) |
| *A24D 3/02* | (2006.01) |
| *A24B 13/00* | (2006.01) |

(52) U.S. Cl.
CPC ............ *A61M 15/06* (2013.01); *B65D 71/06* (2013.01); *B65D 75/04* (2013.01); *B65D 75/5827* (2013.01)

(58) Field of Classification Search
USPC .................................. 131/239, 329; 53/48.4
See application file for complete search history.

(56) References Cited

U.S. PATENT DOCUMENTS

| | | | | |
|---|---|---|---|---|
| 726,629 | A * | 4/1903 | Brown ................... | B65D 39/16 215/364 |
| 2,015,199 | A * | 9/1935 | Sparks .................... | A24F 23/02 383/86 |
| 2,622,594 | A * | 12/1952 | Brooks ................. | A61M 15/08 128/203.15 |
| 3,788,463 | A | 1/1974 | Ruff | |
| 4,841,964 | A * | 6/1989 | Hurka ............... | A61M 15/0028 128/203.15 |
| 5,746,227 | A | 5/1998 | Rose et al. | |
| 5,780,058 | A | 7/1998 | Wong et al. | |
| 6,234,169 | B1 * | 5/2001 | Bulbrook .............. | A61M 15/06 128/203.12 |
| 6,953,040 | B2 * | 10/2005 | Atchley ................. | A24B 13/00 131/352 |
| 2002/0059939 | A1 * | 5/2002 | Fox ....................... | A24F 47/002 131/271 |
| 2003/0041860 | A1 | 3/2003 | Verona | |
| 2005/0106188 | A1 | 5/2005 | Sedaghat Kerdar et al. | |
| 2009/0223999 | A1 * | 9/2009 | Hill .......................... | B65D 1/04 222/129 |
| 2016/0114963 | A1 * | 4/2016 | Reed ........................ | B65B 1/00 220/23.2 |

FOREIGN PATENT DOCUMENTS

| | | | |
|---|---|---|---|
| EP | 1 072 201 A2 | | 1/2001 |
| EP | 1164879 A1 | | 1/2002 |
| GB | 583150 | | 12/1946 |
| GB | 629560 | | 9/1949 |
| GB | 667828 | | 3/1952 |
| GB | 793729 | | 4/1958 |
| GB | 2 118 423 B | | 11/1983 |
| GB | 2 259 695 A | | 3/1993 |
| JP | 02190178 A | * | 7/1990 |
| WO | WO 00/53037 A1 | | 9/2000 |
| WO | WO 02/038208 A3 | | 5/2002 |
| WO | WO 2005/049449 A1 | | 6/2005 |
| WO | WO 2007/135414 A1 | | 11/2007 |
| WO | WO 2011/114946 A1 | | 9/2011 |
| WO | WO 2012/061263 A2 | | 5/2012 |
| WO | WO 2013/174975 A1 | | 11/2013 |

OTHER PUBLICATIONS

Calore, M. (Jun. 19, 2009). Snuff Lures Tobacco Fiends with Whiff of Exotic History. Accessed May 1, 2017. https://www.wired.com/2009/06/snuff/.*
NIST (SI Unit rules and style conventions, The NIST Reference on Constants, Units, and Uncertainty, National Institute of Standards and Technology). (Year: 2004).*
Definition of Pore (Pore, Merriam-Webster Dictionary, https://www.merriam-webster.com/dictionary/pore). (Year: 2018).*
Definition of Perforated (Perforated, Merriam-Webster Dictionary, https://www.merriam-webster.com/dictionary/Perforated). (Year: 2018).*
Notification of Transmittal of International Search Report issued in Application No. PCT/EP2014/061315 dated Nov. 6, 2014 (1 page).
International Search Report issued in Application No. PCT/EP2014/061315 dated Nov. 6, 2014 (6 pages).
Written Opinion of the International Searching Authority issued in Application No. PCT/EP2014/061315 dated Nov. 6, 2014 (10 pages).
Search Report of Great Britain Patent Office issued in Application No. GB1309923.9 dated Oct. 17, 2013 (5 pages).
Search Report of Great Britain Patent Office issued in Application No. GB1407617.8 dated Oct. 28, 2014 (5 pages).

* cited by examiner

DISPENSER FOR PARTICULATE MATERIAL

The present invention relates to inhalers or dispensers for particulate materials such as snuff.

The use of nasal snuff has been known for centuries. Snuff comes in the form of a finely ground, flavoured tobacco and is generally taken by a simple sniff into the nostrils. It is well-known that snuff interactions normally take place in the nasal mucus membranes of the user, and it will be appreciated that the references to 'inhale' or 'inhaler' herein do not mean or imply that the snuff is taken into the users lungs or sinuses.

Various devices are available to facilitate the inhalation of snuff by the user, for example 'snuff snorters' (in the form of a hollow metal tube) and 'snuff bullets', which can be made or plastic, metal or glass. These 'snuff bullets' generally comprise a small bottle connected to a rotatable 'dosing chamber' and an outlet hole at the top. Nowadays, these tend to be the preferred device for snuff users to inhale the product. However, there are hygiene issues with the known devices. Firstly, they need to be cleaned regularly and stored in an appropriately clean condition between uses, because they are placed in the nostril for use. Secondly, snuff users have to physically handle the snuff prior to administration, which poses potential hygiene problems.

There is a need for a snuff inhaler or dispenser product that is disposable, low cost, capable of being manufactured on a mass scale, and which can be kept clean prior to use. Furthermore, it would be desirable for such a product should be able to deliver a reproducible dose of snuff to the user and have a suitably tactile feel in use. In addition, it would be useful if the product could be supplied in packs so that users would be able to share (different items) from the same pack, thereby providing greater social interaction between users.

According to the present invention there is provide a particulate material dispenser (e.g. a snuff dispenser) including a longitudinally extending (e.g. generally cylindrical) body comprising: a longitudinally extending (e.g. generally cylindrical) base element; a (e.g. generally cylindrical) tubular element which extends longitudinally from the base element such that the inner wall of the tubular element defines (e.g. with the base element)
a cavity (or reservoir); and
a particulate material within the cavity or reservoir;
the dispenser optionally including closure means for the cavity or reservoir.

The particulate material dispenser includes particulate material (e.g. snuff) located within the cavity/reservoir. Preferably, the particulate material is snuff. The dose (amount) of particulate (snuff) in the cavity is typically sufficient to give an acceptable delivery in use (when dispensed). The amount of particulate material (snuff) in the cavity may be 0.05 to 0.5 $cm^3$, for example 0.10 $cm^3$ to 0.20 $cm^3$. An acceptable delivery amount (volume) would typically be in the order of 0.15 $cm^3$ per sniff. Preferably, the cavity includes a single dose, for example 0.10 $cm^3$ to 0.20 $cm^3$, preferably 0.15 $cm^3$ of snuff. In other words, a single dose (single use or single sniff) dispenser is preferred.

Preferably, the longitudinally extending body is cylindrical. The external diameter of the body may be from 4 to 15 mm, more preferably 8 to 12 mm. Preferably, the tubular element is cylindrical. The external diameter of the tubular element may be from 4 to 15 mm, more preferably 8 to 12 mm. Preferably, the base element is cylindrical. The external diameter of the base element may be from 4 to 15 mm, more preferably 8 to 12 mm. Preferably the tubular element and the base have the same, or substantially the same, diameter.

The present invention applies technologies used in the manufacture of cigarette filters and filter elements to produce a snuff dispenser or 'snuff inhaler'. The product includes a tubular structure that is closed at one end and has an opening at the other end of the tube. A defined dose of snuff is located within a hollow section (e.g. the cavity) of the tubular structure. A closure means (e.g. a cap or capping member) preferably covers the open end of the dispenser (e.g. tubular element) to ensure that the snuff content does not inadvertently fall out of the cavity (dispenser) prior to use. The user simply removes this cap before inhaling, inserts the open end of the dispenser (device) into the base of their nostril, and dispenses the snuff by sniffing ("snorting", inhaling) the snuff in the customary manner.

The base element and/or tubular element (of the longitudinally extending body) are preferably porous (although this is not essential). The base element and tubular element may be formed from the same material, or from different materials. The base element and the tubular element may be formed separately, or they may be of unitary construction. If the base element and the tubular element are of unitary construction they may be formed by similar methods to those used to make Filtrona Long Bore SAF filters (see EP1164879). The longitudinally extending body may further comprise a common wrapper, which is engaged around the base element and the tubular element. If the base element and the tubular element are not of unitary construction, for example, the common wrapper may serve to hold the base element and the tubular element in place (e.g. abutted against each other). The base element and/or tubular element may be formed from a bonded fibrous structure, from a folded film, paper or nonwoven material, or formed via an extrusion or moulding process. The base element and/or tubular element may, for example, be made of cellulose acetate, polypropylene, polyester, bicomponent fibre, paper or any other similar material. The base element is preferably porous. The base element is preferably formed of a material which has a low pressure drop, for example a pressure drop of 5 to 350 mm water (for a 10 mm length×8 mm diameter element), for example a pressure drop of 5 to 250 mm water (for a 10 mm length×8 mm diameter element), more preferably a pressure drop of 10 to 300 mm water (for a 10 mm length×8 mm diameter element), for example 10 to 200 mm water (for a 10 mm length×8 mm diameter element). The use of a porous material having a low pressure drop may facilitate ease of 'snorting'.

The dispenser may include a closure means (e.g. a cap).

The closure means may be in the form of a sealing tape or sealing disc which is applied to the top of the tubular element (after the snuff has been inserted into the cavity) to hold the snuff in place.

Preferably the closure means (e.g. cap) may be removed (for the dispensing of snuff).

In another example, the closure is a cap comprising a (generally cylindrical) capping element and a generally cylindrical plug element which extends from one face of the capping element. The outer diameter of the plug element is slightly less that the inner diameter of the tubular element such that the plug element may fit snugly within the tubular element. This type of cap could, for example, be made of plastic via an injection moulding process.

In the above examples of the invention the base element and/or tubular element may be formed from a bonded fibrous structure (e.g. cellulosed acetate), from a folded film, paper or nonwoven material, or formed via an extrusion or moulding process. The base element and/or tubular element may, for example, be made of cellulose acetate, polypropylene, polyester, bicomponent fibre, paper or any other similar material. The longitudinally extending (e.g. generally cylindrical) body may further comprise a common wrapper which is engaged around the base element and/or the tubular element.

It will be appreciated that the base element and/or tubular element and/or capping element may be made (and wrapped) in the same well known ways as filter elements/plugs are made for use in tobacco smoke filters. For example, the base element may be made in the same way as (and dimensioned similarly to) a conventional Non Wrapped Acetate filter.

Thus, the dispensers of the invention have the advantage that they can be easily manufactured using technologies known in the cigarette filter manufacturing industry. It is also possible to add the snuff to the device at the same time it is being made rather than in a separate downstream process, through adaptation of known processes used to add granular and particulate material to cigarette filters.

In another example, the longitudinally extending (e.g. generally cylindrical) body includes a longitudinally extending (e.g. generally cylindrical) base element;

a (e.g. generally cylindrical) tubular element which extends longitudinally from the base element, the inner wall of the tubular element defining (e.g. with the base element) a first cavity (or reservoir);

a (e.g. generally cylindrical) capping element which is distanced longitudinally from the end of the tubular element (e.g. the end of the tubular element which is opposite to the base element); and a common outer wrapper which is engaged around the base element, the tubular element and the capping element, the inner wall of the common outer wrapper defining a second cavity (or reservoir) between the tubular element and the capping element.

The common wrapper may include a line of weakness substantially in register with (e.g. in register with, or within 5 mm of, preferably within 2 or 3 mm of) the junction between the (abutted) tubular element and the base element. A particulate material, e.g. snuff, may be located within the first cavity/reservoir and/or the second cavity/reservoir.

According to the present invention in a further aspect there is provided a dispenser for a particulate material (e.g. snuff), the dispenser including a longitudinally extending body comprising:

a longitudinally extending (e.g. generally cylindrical) base element;

a (e.g. generally cylindrical) tubular element which extends longitudinally from the base element, the inner wall of the tubular element defining (e.g. with the base element) a first cavity (or reservoir);

a (e.g. generally cylindrical) capping element which is distanced longitudinally from the end of the tubular element (e.g. the end of the tubular element which is opposite to the base element);

a common outer wrapper which is engaged around the base element, the tubular element and the capping element, the inner wall of the common outer wrapper defining a second cavity (or reservoir) between the tubular element and the capping element; and, optionally, a particulate material (e.g. snuff) within the first and/or second cavity.

The common wrapper may include a line of weakness substantially in register with (e.g. in register with, or within 5 mm of, preferably within 2 or 3 mm of, for example 2 mm from) the junction between the (abutted) tubular element and the base element.

The common wrapper may include a line of weakness substantially in register with the junction between the (abutted) tubular element and the base element, along which the wrapper is snapped or torn to release the base element from the tubular element and reveal the first cavity (and particulate material, e.g. snuff, therein, if present) so the a particulate material (e.g. snuff) can be dispensed. The line of weakness may be in register with the junction between the (abutted) tubular element and the base element, or within 5 mm of, preferably within 3 mm of, for example 2 mm from, the junction between the (abutted) tubular element and the base element. It is preferred that the line of weakness is located over the tubular element. This positioning means that the line of weakness (and the cut) will be below the edge of the (e.g. tubular) element of the dispenser which is e.g. inserted into the e.g. nose of the user, reducing the risk of sharp (paper) edges at the end of the dispenser (and reducing the risk of injury to the user when the dispenser is inserted into e.g. the user's nose.).

The common wrapper may be cellophane or BOPP, but it is preferred that the common wrapper is paper. The line of weakness may be a line of perforations (e.g. holes) in the wrapper. Preferably the line of weakness is a line which has been cut into (but not through) the wrapper, or scored into the wrapper. The line of weakness (e.g. scoring or perforation) indicates to the consumer where the product should be snapped. Preferably the common wrapper is a paper of basis weight from about 40 to 120 gsm, preferably a paper of basis weight 50 to 90 gsm, for example 60 gsm or 80 gsm. The applicants have found that scoring works better when the common product wrapper is a thicker or heavier-weight paper (with the additional advantage that the heavier weight paper also provides a better 'quality' feel to the product). Introduction of the line of weakness (e.g. scoring/perforating) may be carried out either before (to the wrapper) or after the product is assembled (after the wrapper has been engaged around the dispensers) (i.e. in-line).

The outer wrapper may be coloured or pigmented (e.g. black, grey, blue, red, brown or green), and/or may be transparent or transparent in selected regions to enable the user to see the underlying product. The outer wrapper may be printed with a suitable ink (notably black, grey or blue).

The applicants have found that in examples with a first and second cavity, particulate material (e.g. snuff) in the second cavity may be visible, which is not always desirable. In examples of the invention, the outer wrapper may be chosen to render the contents of the dispenser invisible (which may be desirable). For example, the outer wrapper may be of opacity 95% or greater. The outer wrapper is preferably printed with a suitable ink (notably black, grey or blue), e.g. to increase the opacity and thereby disguise the cavity. Printing the paper has the advantage of improving appearance of the outer wrapper but without affecting the runnability of the paper during the manufacturing process. It is also possible to print the outer wrapper on both sides (and/or have the printed surface on the inside or outside of the finished dispenser). In an alternative, the outer wrapper may comprise a foil or other opaque material attached (e.g. laminated) to the paper.

The base element, tubular element and capping element may be formed from a bonded fibrous structure, from a folded film, paper or nonwoven material, or formed via an extrusion or moulding process. The base element and/or tubular element may, for example, be made of cellulose acetate, polypropylene, polyester, bicomponent fibre, paper or any other similar material. The base element is preferably porous. In this example, the capping element is preferably formed of a material which has a low pressure drop, for example a pressure drop of 5 to 350 mm water (for a 10 mm length×8 mm diameter element), for example a pressure drop of 5 to 250 mm water (for a 10 mm length×8 mm diameter element), more preferably a pressure drop of 10 to 300 mm water (for a 10 mm length×8 mm diameter element), for example a pressure drop of 10 to 200 mm water (for a 10 mm length×8 mm diameter element). The use of a porous material having a low pressure drop may facilitate ease of administration of the particulate material (e.g. snuff), e.g. by facilitating suction of the particulate material by the user.

The applicants have found that the inclusion of a first and second cavity facilitates manufacture and filling of the dispensers in a single pass process without requirement for the dispensers to be upright while being filled (see below). Further, the inclusion of a first and second cavity allows increased loading of particulate material (e.g. snuff).

According to the invention, there is provided a method of production of dispensers for particulate material (e.g. snuff), the method comprising the steps of: continuously advancing, longitudinally, a flow of (e.g. individual e.g. pre-formed) longitudinally extending (e.g. substantially cylindrical) rods which are arranged on a longitudinally advancing wrapper substrate between (e.g. pre-formed) longitudinally extending tubular elements, wherein each longitudinally extending (e.g. substantially cylindrical) rod in the advancing flow is arranged with a first end abutted to a first longitudinally extending tubular element, and a second end (e.g. the end opposite to the first end) adjacent to a space (gap) in the advancing flow between the second end of the longitudinally extending (e.g. substantially cylindrical) rod and a second longitudinally extending tubular element in the flow;

introducing a particulate material (e.g. snuff) into each space (gap) between a longitudinally extending (e.g. substantially cylindrical) rod and a longitudinally extending tubular element in the flow;

engaging (and e.g. fixing) the wrapper substrate around the longitudinally advancing flow to thereby form a continuous wrapped product rod comprising a plurality of longitudinally extending (e.g. substantially cylindrical) rods each arranged with a first end abutted to a first longitudinally extending tubular element, and a second end (e.g. the end opposite to the first end) adjacent to an additive containing cavity between the second end of the longitudinally extending (e.g. substantially cylindrical) rod and a second longitudinally extending tubular element.

Optionally, the method may include a further step of cutting the continuous wrapped product rod in register with each longitudinally extending (e.g. substantially cylindrical) rod, to thereby form (individual) dispensers for particulate material (e.g. snuff).

It will be appreciated that each dispenser so formed includes a longitudinally extending body comprising: a longitudinally extending (e.g. generally cylindrical) base element; a (e.g. generally cylindrical) tubular element which extends longitudinally from the base element, the inner wall of the tubular element defining (e.g. with the base element) a first cavity (or reservoir); a (e.g. generally cylindrical) capping element which is distanced longitudinally from the end of the tubular element (e.g. the end of the tubular element which is opposite to the base element); a common outer wrapper which is engaged around the base element, the tubular element and the capping element, the inner wall of the common outer wrapper defining a second cavity (or reservoir) between the tubular element and the capping element; and a particulate material (e.g. snuff) within at least the second cavity.

The applicants have found that the method according to this aspect of the invention allows manufacture and filling of dispensers in a single pass process without requirement for the dispensers to be upright prior to filling and capping.

In an example, the step of introducing the particulate material (e.g. snuff) into each space (gap) between a longitudinally extending (e.g. substantially cylindrical) rod and a longitudinally extending tubular element in the flow is performed while suction (e.g. a vacuum) is applied to the longitudinally extending tubular element which is adjacent to the space. If this is the case it is preferred that the longitudinally extending porous elements are porous. In this example, the suction (vacuum) draws the particulate material (e.g. snuff) into the tubular element as the particulate material (e.g. snuff) is introduced into the space (gap). This example allows increased additive loading because additive [a particulate material (e.g. snuff)] is located in a first cavity (within the tubular element) and the (second) cavity [which is between the second end of the longitudinally extending (e.g. substantially cylindrical) rod and the second longitudinally extending tubular element].

In another example, the step of introducing the particulate material (e.g. snuff) into each space (gap) between a longitudinally extending (e.g. substantially cylindrical) rod and a longitudinally extending tubular element in the flow is performed in the absence of suction or performed while suction (e.g. a vacuum) is applied to the longitudinally extending (e.g. substantially cylindrical) rod which is adjacent to the space. If this is the case it is preferred that the longitudinally extending (e.g. substantially cylindrical) rod is porous. In this example, little or no particulate material (e.g. snuff) is drawn into the tubular element as the particulate material (e.g. snuff) is introduced into the space (gap) [e.g. because the vacuum sucks the particulate material (e.g. snuff) towards the rod and retains the additive within the cavity]. This example limits the additive [particulate material (e.g. snuff)] loading.

The method may include a further step of introducing a line of weakness into the wrapper substantially in register with, or within 5 mm of, the or each junction between abutted tubular elements and rods in the advancing flow. This may be done by methods well known in the art, and referred to herein.

According to the invention in a still further aspect there is provided a product comprising a plurality (e.g. 2, 4, 6) of (discrete, identical or substantially identical) dispensers according to any aspect of the invention (e.g. arranged end-to-end in a mirror image relationship); and a common wrapper engaged around the dispensers. It will be appreciated that these dispensers and products of the invention may be packed in groups (e.g. 10 or 20 products as set out above may be packaged in a carton similar to a cigarette pack), or products and dispensers may be packed individually in blister packs.

According to the invention in a still further aspect there is provided a product comprising two (discrete, identical or substantially identical) dispensers according to any aspect of the invention joined together [for example arranged end-to-end (e.g. base element to base element)]. The product may include a common wrapper engaged around the dispensers.

The present invention will now be illustrated with reference to the following Examples and the attached drawings in which.

Figure 1:
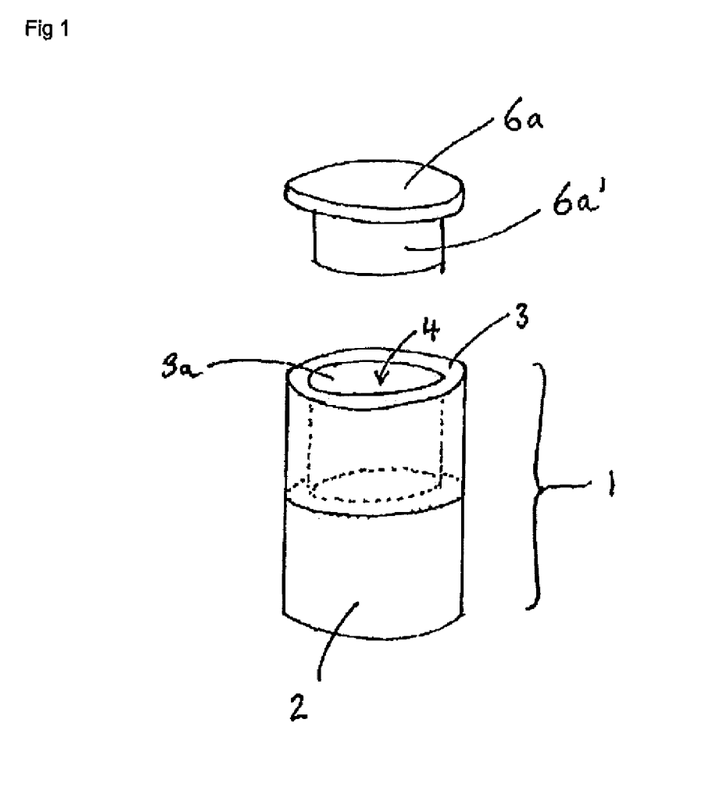
FIG. 1 schematically illustrates (not to scale) a dispenser according to an example of the invention.

FIG. 1 shows a snuff dispenser according to the invention. The snuff dispenser has a longitudinally extending cylindrical body 1 which includes a longitudinally extending cylindrical base element 2 of length 20 mm and external diameter about 8 mm. The base element 2 is made of cellulose acetate and is porous (and of a low pressure drop of around 60 mm water) to facilitate ease of 'snorting'. A cylindrical tubular element 3 is abutted to the base element 2 and extends longitudinally from the base element 2. The tubular element 3 is made of cellulose acetate plasticised with triacetin, as is well-known from cigarette filter manufacture, and is of length 20 mm and external diameter about 8 mm. The inner wall 3a of the tubular element 3 defines, with the upper face of the base element 2, a cavity (reservoir) shown by arrow 4. The cavity 4 is of internal diameter 6 mm and depth 20 mm. The cavity includes a single dose of about 0.15 cm³ of snuff (not shown). The longitudinally extending cylindrical body 1 also includes a common wrapper (not shown) of paper plugwrap, which is engaged around the base element 2 and tubular element 3 and held in place with a lapped and (adhesive) stuck seam. The outer wrapper holds base element 2 and tubular element 3 in place; this type of construction is well-known from cigarette filter manufacture.

FIG. 1 also shows closure means in the form of a cap. In FIG. 1 the cap has been removed from the tubular body 1. The cap comprises a cylindrical capping element 6a and a generally cylindrical plug element 6a' which extends from one face of the capping element 6. The capping element 6a and plug element 6a' are of length 5 mm in total and formed in one piece from plastic via an injection moulding process. As can be seen in FIG. 1, the outer diameter of the plug element 6a' is slightly less that the inner diameter of the tubular element 3 such that the plug element 6a' may fit snugly within the tubular element 3. The plug element 6a' may be inserted into the open end of tubular element 3 (i.e. the end of tubular element 3 opposite to the base element 2) to plug the cavity 4 to thereby help retain the snuff contents in place, and keep the end of the body 1 in a clean condition. The outer diameter of the plug element 6a' is slightly less that the inner diameter of the tubular element 3, so there is a snug interference fit between the outer face of the plug element 6a' and the inner wall of the tubular element 3a. This means that the cap is held in place, but can be readily removed when the snuff is to be inhaled.

This means that the cap is held in place, but can be readily removed when the snuff is to be inhaled.

In use, the user places the open end of the tube in or near the base of their nostril and 'snorts' or inhales the snuff.

Figure 2:
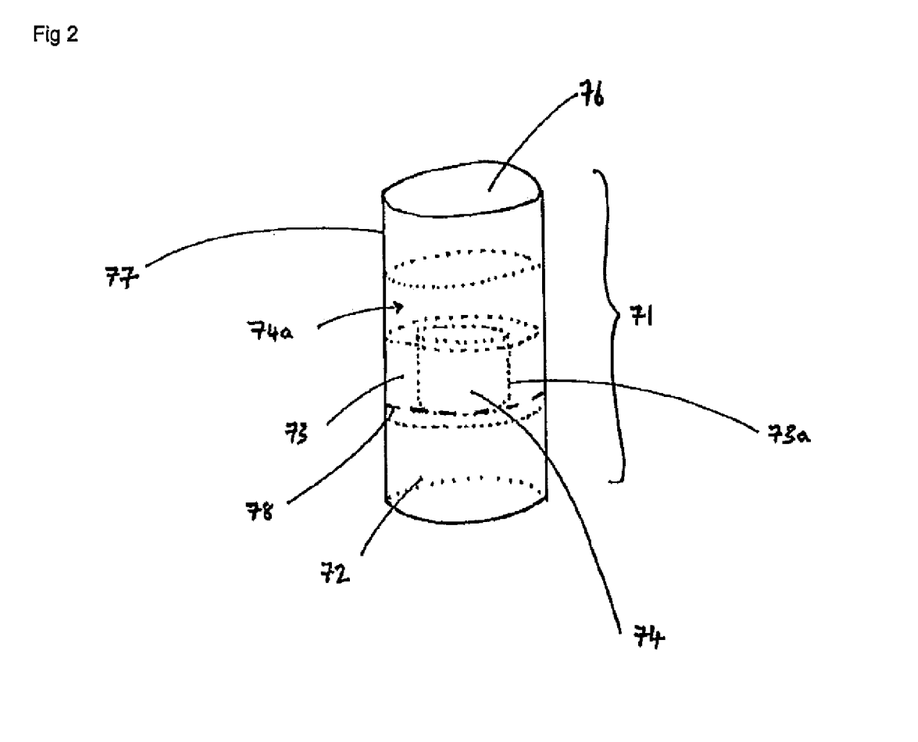
FIG. 2 schematically illustrates (not to scale) a dispenser according to a different example of the invention.

FIG. 2 shows a dispenser according to another example of the invention. The dispenser has a longitudinally extending cylindrical body 71 of length 82 mm and circumference 24.3 mm which includes a longitudinally extending cylindrical base element 72 of length 26 mm and external diameter about 7.6 mm. The base element 72 is made of cellulose acetate and is porous (and of a pressure drop of around 120 mm water). A cylindrical tubular element 73 extends longitudinally from the base element 72. The cylindrical tubular element 73 is abutted to the base element 72 and extends longitudinally from the base element 72. The tubular element 73 is made of cellulose acetate plasticised with triacetin, as is well-known from cigarette filter manufacture, and is of length 12 mm and external diameter about 7.6 mm. The inner wall 73a of the tubular element 73 defines, with the upper face of the base element 72, a first cavity (reservoir) within the tubular element shown by numeral 74. The first cavity 74 is of internal diameter about 4 mm and depth 12 mm. The first cavity includes a single dose of about 0.15 cm³ of snuff (particulate material) in the form of powder (not shown). The dispenser also includes a longitudinally extending capping element 76 of length 40 mm and external diameter about 7.6 mm. The capping element 76 is made of cellulose acetate and is porous (and of a pressure drop of around 180 mm water) to facilitate ease of dispensing of the snuff (particulate material). The capping element 76 is distanced longitudinally from the end of the tubular element 73 (i.e. distanced longitudinally from the end of tubular element which is opposite to the base element), so there is a distance of 4 mm between the capping element 76 and the tubular element 73. The longitudinally extending cylindrical body 71 also includes a common outer wrapper 77 of paper plugwrap of basis weight 80 gsm, which is engaged around the base element 72, tubular element 73 and capping element 76 and held in place with a lapped and (adhesive) stuck seam to hold elements 72, 73 and 76 in place such that the inner wall of the common outer wrapper 77 defines a second cylindrical cavity (or reservoir) 74a, of diameter approximately 7.6 mm and depth 4 mm, between the tubular element and the capping element. The common wrapper includes a line of weakness 78 (shown by dashed line in FIG. 2) around the circumference of the longitudinally extending body 71 located around 2 mm from the junction between the (abutted) tubular element and the base element, along which the wrapper is snapped or torn to release the base element from the tubular element and reveal the first cavity so the snuff can be dispensed. The line of weakness 78 is located over the tubular element. This positioning means that the line of weakness (and the cut) will be below the edge of the (e.g. tubular) element of the dispenser which is e.g. inserted into the e.g. nose of the user, reducing the risk of sharp edges at the end of the dispenser (and reducing the risk of injury to the user when the dispenser is inserted into e.g. the user's nose etc.). The outer wrapper is printed with a suitable ink (notably black, grey or blue), e.g. to increase the opacity and thereby disguise the second cavity and snuff therein. Printing the paper has the advantage of improving appearance of the outer wrapper but without affecting the runnability of the paper during the manufacturing process.

The user grasps the 26 mm long base element 72 and pulls or snaps it so that it breaks at the perforations, so the base element 72 can be removed to expose the end of the tubular element 73. It will be appreciated that the exposed end of the tubular element 73 is the end of the tubular element which is opposite the cavity 74a. The user may then discard the base element and hold the remainder of the dispenser to dispense the snuff through the exposed end of the tubular element 73.

Figure 3:
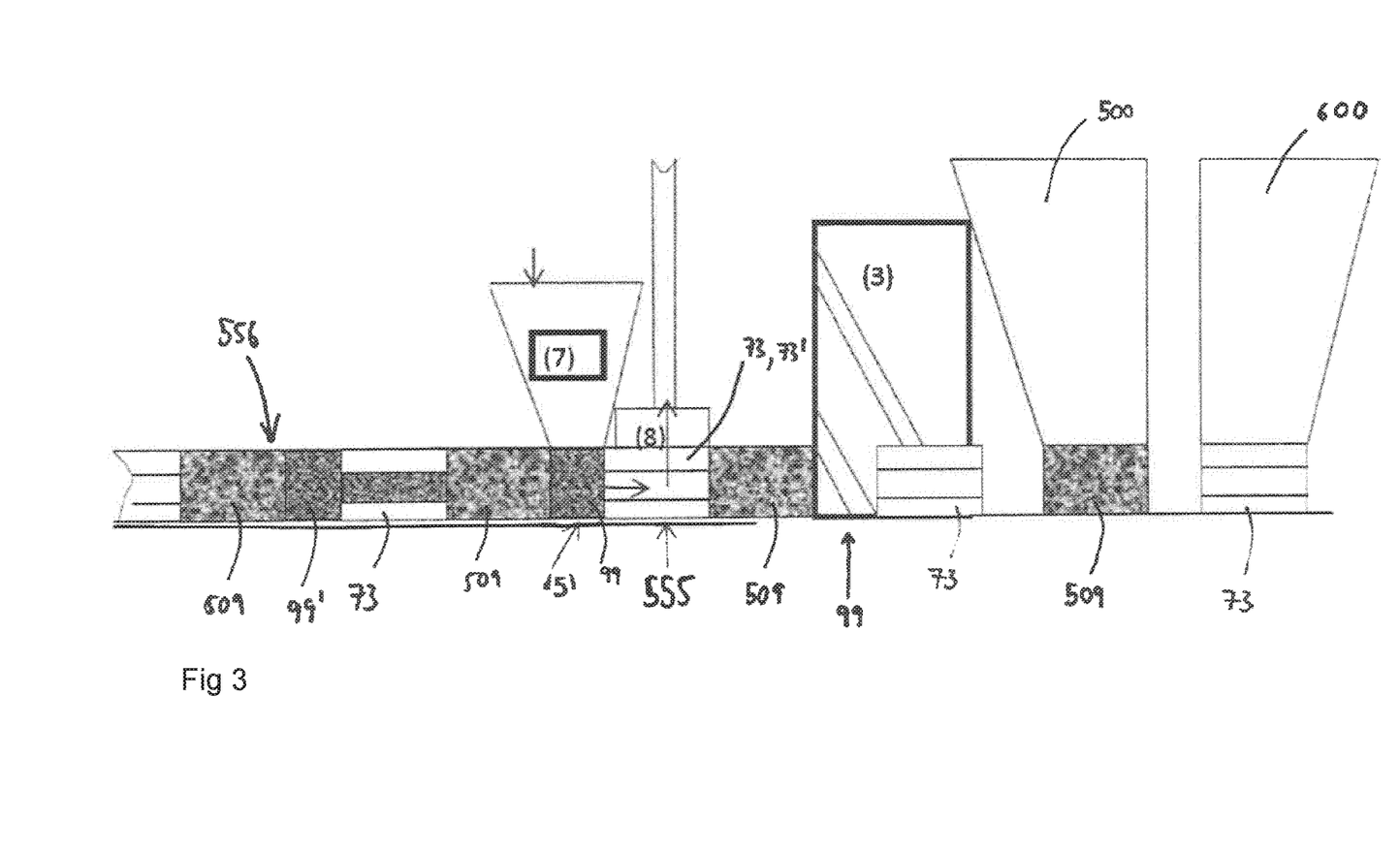
FIG. 3 illustrates apparatus for manufacturing the dispensers shown in FIG. 2.

FIG. 3 shows an apparatus for making the dispensers of FIG. 2 in a continuous process according to a further embodiment of the invention, which uses conventional cigarette filter making machinery.

As shown in FIG. 3 a first hopper 500 releases individual pre-formed longitudinally extending substantially cylindrical rods 509, formed from cellulose acetate, and each of length 66 mm. A second hopper 600 releases pre-formed longitudinally extending tubular elements 73 cut to length 12 mm, which are formed of cellulose acetate plasticised with triacetin, and are porous. Hoppers 500 and 600 release rods 509 and tubular elements 73 respectively to form a continuously longitudinally advancing flow of alternating rods 509 and tubular elements 73 which advances in the direction of arrow 510.

The rods 509 and tubular elements 73 are picked up by a collator drum (3), with the collator drum "pushing" on rods 509 such that the rod is pushed such that each longitudinally extending (e.g. substantially cylindrical) rod 509 in the advancing flow is arranged with a first end abutted to a longitudinally extending tubular element 73, and its second end (the end opposite to the first end) adjacent to a space (gap) 99 in the advancing flow between the second end of the longitudinally extending (e.g. substantially cylindrical) rod 509 and a second longitudinally extending tubular element 73 in the flow. This process forms a continuously advancing, longitudinally, flow of (e.g. individual e.g. preformed) longitudinally extending (e.g. substantially cylindrical) rods 509 which are arranged between (e.g. preformed) longitudinally extending tubular elements 73, wherein each longitudinally extending (e.g. substantially cylindrical) rod 509 in the advancing flow is arranged with a first end abutted to a first longitudinally extending tubular element 73, and a second end (e.g. the end opposite to the first end) adjacent to a space (gap) 99 in the advancing flow between the second end of the longitudinally extending (e.g. substantially cylindrical) rod 509 and a second longitudinally extending tubular element 73 in the flow.

As shown in FIG. 3, the longitudinally advancing flow enters a garniture 555 where it becomes entrained on a longitudinally advancing wrapper substrate in the form of a paper of basis weight 80 gsm, which may be printed (e.g. with blue ink). As can be seen in FIG. 3, the flow is arranged on a longitudinally advancing wrapper substrate in the following order: rod 509+cavity 99+tubular element 73+rod 509 and so on.

The particulate material (5) (e.g. snuff) is introduced into each space (gap) 99 between a longitudinally extending (e.g. substantially cylindrical) rod 509 and a longitudinally extending tubular element 73 in the flow, using a Hamburg shoe (7), which drops the additive (snuff) using gravity and/or use of a vibrating device where required.

In the illustrated example, the step of introducing the particulate additive (e.g. snuff) into each space (gap) 99 between a longitudinally extending (e.g. substantially cylindrical) rod 509 and a longitudinally extending tubular element 73 in the flow is performed while suction (e.g. a vacuum) is applied to the longitudinally extending tubular element 73' which is adjacent to the space 99, by suction means (8). In the illustrated example, the suction means is upstream of the Hamburg shoe. The suction means [inlet (8)] removes excess powdered/particulate additive (e.g. snuff) (5), and at the same time creates a vacuum over the tubular element 73', which is porous. The suction (vacuum) draws the particulate additive (e.g. snuff) (5) into the hollow part of the tubular element 73' as the particulate additive (e.g. snuff) is introduced into the space (gap) 99. This example allows increased additive loading because additive is located in a first cavity (within the tubular element) and the (second) cavity 99 [which is between the second end of the longitudinally extending (e.g. substantially cylindrical) rod and the second longitudinally extending tubular element].

The garniture engages (and fixes) the wrapper substrate around the longitudinally advancing flow, by methods well known in the art of making tobacco smoke filters, to thereby form a continuous wrapped product rod 556 comprising a plurality of longitudinally extending (e.g. substantially cylindrical) rods 509 each arranged with a first end abutted to a first longitudinally extending tubular element 73, and a second end (e.g. the end opposite to the first end) adjacent to an additive [particulate additive (e.g. snuff)] containing cavity 99' between the second end of the longitudinally extending (e.g. substantially cylindrical) rod 509 and a second longitudinally extending tubular element 73.

The continuous wrapped product rod may then be cut (by a rotary knife or similar). The continuous wrapped rod may be cut in register with the (each) rod 509 (at a position 40 mm along each rod) such that the product rod is cut into individual dispensers as shown in FIG. 2. The continuous wrapped product rod is cut in register with each longitudinally extending (e.g. substantially cylindrical) rod 509, to thereby form (individual) dispensers 71 for particulate additive (e.g. snuff). It will be appreciated that each dispenser 71 so formed includes a longitudinally extending body comprising: a longitudinally extending (e.g. generally cylindrical) base element 72; a (e.g. generally cylindrical) tubular element 73 which extends longitudinally from the base element, the inner wall of the tubular element defining (e.g. with the base element) a first cavity (or reservoir); a (e.g. generally cylindrical) capping element 76 which is distanced longitudinally from the end of the tubular element 73 (e.g. the end of the tubular element which is opposite to the base element); a common outer wrapper 77 which is engaged around the base element, the tubular element and the capping element, the inner wall of the common outer wrapper defining a second cavity (or reservoir) between the tubular element and the capping element; and a particulate additive (e.g. snuff) within at least the second cavity. It will be appreciated that base element 72 and capping element 76 are formed the rod 509 by cutting the rod 509 into two.

It will be appreciated that in the above method the resulting rod may have both the cavity and the tubular element filled with the powdered (particulate) material, snuff (because of suction applied to the tubular element 73 while the cavity is being filled).

It will be appreciated that a line of weakness may be introduced into the wrapper substantially in register with, or within 5 mm of, the or each junction between abutted tubular elements 73 and rods 509 in the advancing flow, by methods well known in the art.

In another example, the step of introducing the particulate additive (e.g. snuff) into each space (gap) between a longitudinally extending (e.g. substantially cylindrical) rod and a longitudinally extending tubular element in the flow is performed in the absence of suction or performed while suction (e.g. a vacuum) is applied to the longitudinally extending (e.g. substantially cylindrical) rod which is adjacent to the space. In this example, little or no particulate additive (e.g. snuff) is drawn into the tubular element as the particulate additive (e.g. snuff) is introduced into the space (gap) [e.g. because the vacuum sucks the particulate additive (e.g. snuff) towards the rod and retains the additive within the cavity]. This example limits the additive loading. Thus, in order to avoid (or minimise) the filling of the tubular element with particulate material, with the illustrated apparatus, the feeding order of segments by the collator drum (3) would be changed (not shown) such that the order entering the garniture 555 is: rod 509+tubular element 73+cavity 99+rod 509, etc. This means that, for the apparatus, the tubular element would be downstream of the suction inlet as the cavity 99 is being filled, and the suction inlet is located over a rod 509. This means that when the cavity 99 is filled, powdered/particulate material does not enter the inside of the tubular element 73 (because it is being sucked upstream towards the rod 509 over which the suction means is placed). The position of the later cutting (along the rods 509) may also be adjusted, by methods known in the art, such that a mirror version of the product is obtained. Thus, the apparatus of FIG. 3 can be adapted so dispensers 71 may be formed, either with or without particulate material in the tubular element.

The hoppers, garniture, Hamburg shoe, suction device etc. are all well known in the tobacco smoke filter making art.

A key advantage of the FIG. 2 and FIG. 3 product/process in particular is that the dispensers may be made on standard tobacco smoke filter making equipment rather than requiring special processes where the tube section needs to be held in a vertical orientation to enable the tube section to be filled.

The invention claimed is:

1. A particulate material dispenser including a longitudinally extending body comprising:
    a longitudinally extending base element;
    a tubular element extending longitudinally from the base element such that an inner wall of the tubular element defines a first cavity;
    a capping element which is distanced longitudinally from an end of the tubular element;
    a common outer wrapper which is engaged around the base element, the tubular element and the capping element, the inner wall of the common outer wrapper defining a second cavity between the tubular element and the capping element; and
    snuff within both the first cavity and the second cavity; wherein the base element and/or the tubular element is porous.

2. The dispenser according to claim 1 wherein the amount of particulate material is 0.10 cm$^3$ to 0.20 cm$^3$.

3. The dispenser according to claim 1 wherein the longitudinally extending body is a cylinder of external diameter 4 to 15 mm.

4. The dispenser according to claim 1 wherein the base element and the tubular element are of unitary construction.

5. The dispenser according to claim 1 wherein the common wrapper includes a line of weakness substantially in register with a junction between the tubular element and the base element.

6. A product comprising a plurality of dispensers according to claim 1 arranged end-to-end in a mirror image relationship; and a common wrapper engaged around the dispensers.

7. A product comprising two dispensers according to claim 1 joined together.

8. The product according to claim 7 wherein the dispensers are arranged base element to base element.

* * * * *